United States Patent
Miyamoto et al.

(10) Patent No.: US 9,029,599 B2
(45) Date of Patent: May 12, 2015

(54) PROCESS FOR PRODUCING (METH)ACRYLIC ACID

(71) Applicant: Nippon Shokubai Co., Ltd., Osaka (JP)

(72) Inventors: Takashi Miyamoto, Hyogo (JP); Yoshitake Ishii, Hyogo (JP); Toyofumi Sakai, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 112 days.

(21) Appl. No.: 14/016,439

(22) Filed: Sep. 3, 2013

(65) Prior Publication Data

US 2014/0066652 A1 Mar. 6, 2014

(30) Foreign Application Priority Data

Sep. 6, 2012 (JP) .................................. 2012-196475
Aug. 27, 2013 (JP) .................................. 2013-175932

(51) Int. Cl.
*C07C 51/43* (2006.01)

(52) U.S. Cl.
CPC ...................................... *C07C 51/43* (2013.01)

(58) Field of Classification Search
None
See application file for complete search history.

(56) References Cited

U.S. PATENT DOCUMENTS

| 5,935,534 A | 8/1999 | Umino et al. |
| 2012/0071620 A1 | 3/2012 | Sakamoto et al. |
| 2012/0108847 A1 | 5/2012 | Sakamoto et al. |

FOREIGN PATENT DOCUMENTS

| EP | 2 450 340 | 5/2012 |
| JP | 9-155101 | 6/1997 |
| WO | 2010/140530 | 12/2010 |

OTHER PUBLICATIONS

Extended Search Report issued Mar. 28, 2014, in corresponding European Application No. 13004284.9.

*Primary Examiner* — Karl J Puttlitz
(74) *Attorney, Agent, or Firm* — Wenderoth, Lind & Ponack, L.L.P.

(57) ABSTRACT

A process for producing (meth)acrylic acid comprising the step of repeating a crystallization operation "n" times to produce purified (meth)acrylic acid from crude (meth)acrylic acid, wherein: the each crystallization operation comprises a crystallizing step and a melting step; a polymerization inhibitor is not added to a (meth)acrylic acid melt obtained in the melting step of the first to $n-1^{th}$ crystallization operation(s) and a (meth)acrylic acid solution subjected to the crystallizing step of the second to $n^{th}$ crystallization operation(s); and a concentration of a polymerization inhibitor in a (meth)acrylic acid solution subjected to the crystallizing step of the first crystallization operation is adjusted so that a concentration of the polymerization inhibitor in a (meth)acrylic acid solution subjected to the crystallizing step of the $n^{th}$ crystallization operation is 2 ppm by mass or higher.

10 Claims, 1 Drawing Sheet

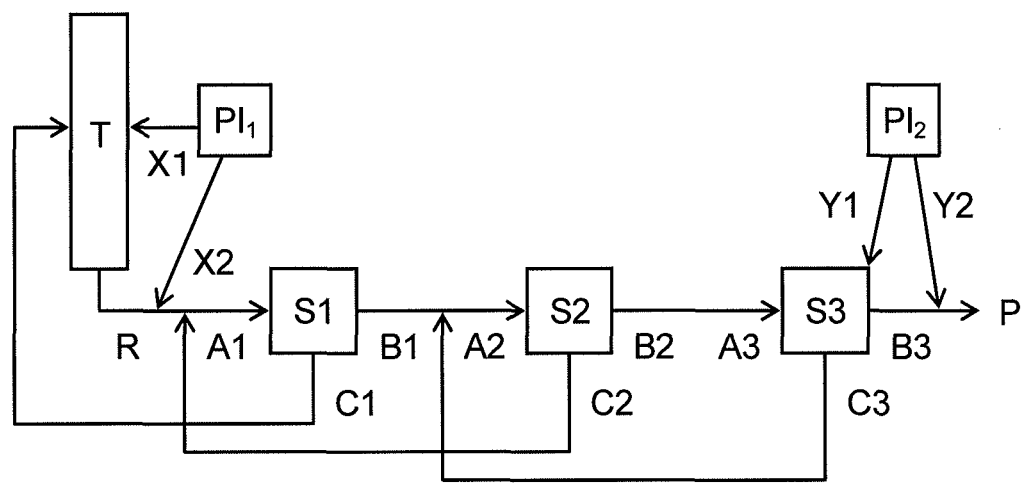

PROCESS FOR PRODUCING (METH)ACRYLIC ACID

BACKGROUND OF THE INVENTION

1. Field of the Invention

The present invention relates to a process for producing (meth)acrylic acid having crystallization operations.

2. Description of the Related Art

Conventionally, a process for producing purified (meth) acrylic acid from crude (meth)acrylic acid by purifying using a crystallization method has been known. In purifying the crude (meth)acrylic acid by crystallization, the crude (meth) acrylic acid is crystallized and the crystallized (meth)acrylic acid is melted, thereby obtaining the purified (meth)acrylic acid. On this occasion, it is preferred that a crystallization operation comprising a crystallizing step and a melting step is repeated multiple times for enhancing purity of the obtained purified (meth)acrylic acid.

(Meth)acrylic acid is known as a polymerizable substance, and there is a case that a polymerization inhibitor is added in the crystallization operation for preventing (meth)acrylic acid polymerization. For example, WO 2010/140530 (Patent Literature 1) discloses a process for producing purified (meth)acrylic acid comprising a melting step in which a (meth)acrylic acid crystal is melted by supplying a melt, to which a polymerization inhibitor has been added, to the (meth)acrylic acid crystal while circulating. In the process disclosed in the Patent Literature 1, the crystallization operation is repeated multiple times, and a polymerization inhibitor is added in the melting step of the last crystallization operation that is for obtaining the purified (meth)acrylic acid as a commercial product and a polymerization inhibitor is further added in the melting step of the preceding crystallization operation. Japanese Unexamined Laid-open Patent Application Publication No. 9-155101 (Patent Literature 2) also discloses a process for producing purified (meth)acrylic acid by repeating the crystallization operation multiple times. In the process disclosed in the Patent Literature 2, (meth)acrylic acid solution which has been prepared by adding a polymerization inhibitor to (meth)acrylic acid melt obtained by the $k+1^{th}$ crystallization operation is added in the melting step of the $k^{th}$ crystallization operation, and purified (meth)acrylic acid, to which a polymerization inhibitor has been added, is also added in the melting step of the last crystallization operation that is for obtaining the purified (meth)acrylic acid as a commercial product.

SUMMARY OF INVENTION

As disclosed in the Patent Literatures 1 and 2, in the case where purified (meth)acrylic acid is prepared from crude (meth)acrylic acid by repeating the crystallization operation multiple times, the crystallization operation is likely to be complicated since a polymerization inhibitor is added at a multiple points.

The present invention has been achieved in view of the above circumstances, and the object of the present invention is to provide a process for producing (meth)acrylic acid that enables easily preventing (meth)acrylic acid polymerization in producing purified (meth)acrylic acid from crude (meth) acrylic acid by repeating a crystallization operation multiple times.

The present inventors have examined extensively and found that (meth)acrylic acid polymerization could be prevented easily in crystallization operations by making a (meth) acrylic acid solution subjected to a crystallizing step of the first crystallization operation to contain a polymerization inhibitor preliminarily so that a concentration of the polymerization inhibitor in a (meth)acrylic acid solution subjected to a crystallizing step of the last crystallization operation is a predetermined value or higher. That is, a process for producing (meth)acrylic acid of the present invention comprises the step of repeating a crystallization operation "n" times to produce purified (meth)acrylic acid from crude (meth)acrylic acid, provided that the "n" is an integer 2 or more, wherein: the each crystallization operation comprises a crystallizing step of supplying a (meth)acrylic acid solution to a crystallizer to obtain a (meth)acrylic acid crystal, and a melting step of melting the (meth)acrylic acid crystal to obtain a (meth) acrylic acid melt; a polymerization inhibitor is not added to the (meth)acrylic acid melt obtained in the melting step of the first to $n-1^{th}$ crystallization operation(s) and the (meth) acrylic acid solution subjected to the crystallizing step of the second to $n^{th}$ crystallization operation(s); and a concentration of a polymerization inhibitor in the (meth)acrylic acid solution subjected to the crystallizing step of the first crystallization operation is adjusted so that a concentration of the polymerization inhibitor in the (meth)acrylic acid solution subjected to the crystallizing step of the nth crystallization operation is 2 ppm by mass or higher.

According to the process for producing (meth)acrylic acid of the present invention, the (meth)acrylic acid solution subjected to the crystallizing step of the first crystallization operation is made to contain a polymerization inhibitor in the amount required for preventing (meth)acrylic acid polymerization in the crystallization operation; and hence, an addition point of the polymerization inhibitor is reduced at minimum, thereby simplifying the crystallization operation, while (meth)acrylic acid polymerization is prevented.

The crystallization operation may further comprise a sweating step of partially-melting the (meth)acrylic acid crystal to obtain a sweated liquid and discharging the sweated liquid from the crystallizer prior to the melting step, and in this case, it is preferred that a polymerization inhibitor is not added to the sweated liquid obtained in the sweating step of the first to $n^{th}$ crystallization operations, too.

It is preferred that the concentration of the polymerization inhibitor in the (meth)acrylic acid solution subjected to the crystallizing step of the first crystallization operation is adjusted higher as the number of times "n" increases. The number of times "n" is preferably 2, 3 or 4 in view of reducing the addition amount of the polymerization inhibitor, and especially, the number of times "n" is more preferably 3, considering the balance between reducing the addition amount of the polymerization inhibitor and ensuring purity of the purified (meth)acrylic acid.

The crude (meth)acrylic acid is preferably obtained by introducing (meth)acrylic acid-containing gas into a collection column to be contacted with a liquid medium, and on this occasion, it is preferred that the polymerization inhibitor is supplied to the collection column to adjust the concentration of the polymerization inhibitor in the (meth)acrylic acid solution subjected to the crystallizing step of the first crystallization operation. Since the polymerization inhibitor supplied to the collection column is discharged from the collection column accompanied by the crude (meth)acrylic acid, supplying the polymerization inhibitor to the collection column provides the effect of preventing polymerization in the crystallization operation as well as that in the collection column.

According to the process for producing (meth)acrylic acid of the present invention, (meth)acrylic acid polymerization can be easily prevented in producing purified (meth)acrylic acid from crude (meth)acrylic acid by repeating the crystallization operation multiple times.

BRIEF DESCRIPTION OF THE DRAWING

FIG. 1 shows an example of a schematic flow of a process for producing (meth)acrylic acid of the present invention.

DESCRIPTION OF THE PREFERRED EMBODIMENTS

A process for producing (meth)acrylic acid of the present invention is for producing purified (meth)acrylic acid from crude (meth)acrylic acid by repeating a crystallization operation "n" times in each of which a (meth)acrylic acid melt is obtained from a (meth)acrylic acid solution, wherein the "n" is an integer 2 or more. The each crystallization operation comprises a crystallizing step of supplying a (meth)acrylic acid solution to a crystallizer to obtain a (meth)acrylic acid crystal, and a melting step of melting the (meth)acrylic acid crystal to obtain a (meth)acrylic acid melt. The crystallization operation may further comprises a sweating step of partially-melting the (meth)acrylic acid crystal to obtain a sweated liquid and discharging the sweated liquid from the crystallizer prior to the melting step, for the purpose of enhancing the purity of the (meth)acrylic acid melt obtained in the melting step. In this case, the crystallization operation comprises the step of a crystallizing step of supplying a (meth)acrylic acid solution to a crystallizer to obtain a (meth)acrylic acid crystal, a sweating step of partially-melting the (meth)acrylic acid crystal to obtain a sweated liquid and discharging the sweated liquid from the crystallizer, followed by a melting step of melting the (meth)acrylic acid crystal to obtain the (meth)acrylic acid melt. In the present invention, a (meth)acrylic acid solution containing the crude (meth)acrylic acid is subjected to the crystallizing step of the first crystallization operation and the (meth)acrylic acid melt obtained by the melting step of the $n^{th}$ crystallization operation is recovered as the purified (meth)acrylic acid.

No particular limitation is placed on the crude (meth)acrylic acid, and the crude (meth)acrylic acid can be any solution containing (meth)acrylic acid and impurities thereof Examples of the impurity include unreacted (meth)acrylic acid production raw materials, water, acetic acid, propionic acid, maleic acid, acetone, acrolein, furfural, formaldehyde, a collection liquid medium and the like. The crude (meth)acrylic acid preferably has a (meth)acrylic acid concentration of 80 mass % or higher, more preferably 83 mass % or higher, and even more preferably 86 mass % or higher.

The crystallization operation is properly conducted by using a crystallizer. Any crystallizer can be used as long as the crystallizer is capable of crystallizing the (meth)acrylic acid solution and melting crystallized (meth)acrylic acid to obtain the (meth)acrylic acid melt. Examples of the crystallizer include, for example, a crystallizer having a heat-transfer surface, wherein the (meth)acrylic acid solution is crystallized and melted by heat-exchange via the heat-transfer surface. As the crystallizer having a heat-transfer surface, an apparatus used as a heat exchanger generally can be employed. For example, a plate-type heat exchanger, a multitubular (shell-and-tube) heat exchanger, a double-pipe heat exchanger, a coil heat exchanger, a spiral plate exchanger or the like can be employed.

The crystallizer is preferably capable of so-called dynamic crystallization in which the (meth)acrylic acid solution is crystallized while the (meth)acrylic acid solution is made to flow downward in the form of a film (Falling Film type). As such crystallizer, a layer-crystallization apparatus made by Sulzer Chemtech Ltd. of Switzerland or the like can be employed.

In the crystallizing step, the (meth)acrylic acid solution is supplied to a crystallizer to be cooled, thereby forming a (meth)acrylic acid crystal. In the case where the crystallizing step is conducted by using a crystallizer having a heat-transfer surface, (meth)acrylic acid may be crystallized by supplying the (meth)acrylic acid solution to one side of the heat-transfer surface while supplying a cooling medium to an other side of the heat-transfer surface to cool the (meth)acrylic acid solution by heat-exchange via the heat-transfer surface.

In the crystallizing step, the (meth)acrylic acid solution only has to be cooled at a temperature lower than its freezing point, and the temperature is not limited as long as (meth)acrylic acid is crystallized in a desired amount. In the case that the (meth)acrylic acid solution is cooled by a cooling medium in the crystallizer having a heat-transfer surface, temperature of the cooling medium is regarded as the cooling temperature of the (meth)acrylic acid solution.

In the crystallizing step, it is preferred that the (meth)acrylic acid solution is cooled to be crystallized while the (meth)acrylic acid solution is circulated. Thus, it is preferred that a circulation path is mounted on the crystallizer and (meth)acrylic acid is crystallized by cooling while circulating the (meth)acrylic acid solution between the crystallizer and the circulation path. In the case of using the Falling Film type crystallizer, a circulation path connecting a lower part of the crystallizer to an upper part of the crystallizer is provided, and the (meth)acrylic acid solution may be discharged from the lower part of the crystallizer and returned to the upper part of the crystallizer. By conducting the crystallizing in this manner, (meth)acrylic acid can be efficiently crystallized.

In the crystallizing step, it is preferred that all of the (meth)acrylic acid solution is not crystallized and a part of the (meth)acrylic acid solution remains uncrystallized. Thus, in the crystallizing step, it is preferred that the (meth)acrylic acid solution is supplied to the crystallizer to obtain a residual mother liquid, an uncrystallized (meth)acrylic acid solution, as well as the (meth)acrylic acid crystal. The residual mother liquid is discharged from the crystallizer in the crystallizing step or the sweating step. In the case where the residual mother liquid is discharged to out of the system in the sweating step, it is efficient that the residual mother liquid is discharged from the crystallizer together with a sweated liquid generated in the sweating step.

In the crystallizing step, 50 mass % to 95 mass % of the (meth)acrylic acid solution which has been supplied to the crystallizer is preferably crystallized, and more preferably, 60 mass % to 90 mass % of that is crystallized. When the crystallized percent of the (meth)acrylic acid solution is in such a range, both the purity and yield of the (meth)acrylic acid crystal can be efficiently enhanced.

In the sweating step, the (meth)acrylic acid crystal formed in the crystallizing step is heated and a sweated liquid obtained by melting a part of the (meth)acrylic acid crystal is discharged from the crystallizer. In the sweating step, impurities present between the crystals or on the surface of the crystal of the (meth)acrylic acid crystal are removed, and the (meth)acrylic acid melt with higher purity can be obtained in the melting step following the sweating step.

In the case where the sweating step is conducted by using a crystallizer having a heat-transfer surface, the (meth)acrylic acid crystal may be heated to be melted by heat-exchange via the heat-transfer surface, where a heating medium is supplied to the other side of the heat-transfer surface as the (meth)acrylic acid crystal presents on the one side of heat-transfer surface. The melting step is also performed essentially in the same manner as the sweating step.

Temperature at which the (meth)acrylic acid crystal is heated in the sweating step is not limited as long as it is a temperature at which the (meth)acrylic acid crystal melts; however, the temperature is preferably about its melting point, since significantly-high temperature to the melting point of (meth)acrylic acid causes wholly-melting of the (meth)acrylic acid crystal, resulting in impairing a sweating effect. Impurities exude from the (meth)acrylic acid crystal by melting the (meth)acrylic acid crystal; and when the (meth)acrylic acid crystal is heated to about the melting point of (meth)acrylic acid at once, the (meth)acrylic acid crystal melts rapidly, that is not preferable. Therefore, in the sweating step, it is preferred that the temperature is raised slowly from below the melting point.

In the melting step, the (meth)acrylic acid crystal only has to be heated at temperature equal to or higher than its melting point; and the temperature is preferably 20° C. or higher, more preferably 25° C. or higher for efficiently melting the (meth)acrylic acid crystal.

Regarding the upper limit of the heating temperature in the sweating step and the melting step, it is preferably 45° C. or lower, more preferably 40° C. or lower for preventing polymerization reaction of (meth)acrylic acid and enhancing the purity or yield of the obtained (meth)acrylic acid melt. In the case that the (meth)acrylic acid crystal is heated by a heating medium in the crystallizer having a heat-transfer surface, temperature of the heating medium is regarded as the heating temperature.

In the sweating step, 0.01 mass % to 30 mass % of the (meth)acrylic acid crystal is preferably melted, and more preferably 0.1 mass % to 10 mass % of that is melted. When a part of the (meth)acrylic acid crystal is melted in such a percentage, the purity and yield of the (meth)acrylic acid melt obtained in the melting step can be effectively enhanced.

The sweated liquid obtained by partially-melting of the (meth)acrylic acid crystal is discharged from the crystallizer. The sweated liquid discharged from the crystallizer may be used as the (meth)acrylic acid solution to be fed to another crystallization step; or the sweated liquid may be returned to any step preceding the crystallization. Examples of the step preceding the crystallization include a collection step, a condensation step, a purification step and the like, that are described below. The residual mother liquid generated in the crystallizing step may be treated similarly to the sweated liquid. Accordingly, the sweated liquid and the residual mother liquid are discharged from the crystallizer preceding the melting step.

In the melting step, the (meth)acrylic acid crystal formed in the crystallizing step is heated to obtain a (meth)acrylic acid melt. By conducting the melting step, the (meth)acrylic acid melt which is purer than the (meth)acrylic acid solution can be obtained. In the melting step, it is preferred that all of the (meth)acrylic acid crystal which has not been melted in the sweating step is melted.

In the melting step, it is preferred that the (meth)acrylic acid crystal is melted while the (meth)acrylic acid melt is circulated. Thus, it is preferred that a circulation path is mounted on the crystallizer and the (meth)acrylic acid crystal is melted by heating while circulating the (meth)acrylic acid melt between the crystallizer and the circulation path. In the case of using the Falling Film type crystallizer, a circulation path connecting a lower part of the crystallizer to an upper part of the crystallizer is provided, and the (meth)acrylic acid melt may be discharged from the lower part of the crystallizer and returned to the upper part of the crystallizer. By conducting the melting in this manner, (meth)acrylic acid crystal can be efficiently melted.

In the producing process of the present invention, a crystallization operation comprising the crystallizing step and the melting step is repeated "n" times to produce the purified (meth)acrylic acid from the crude (meth)acrylic acid, wherein the "n" is an integer 2 or more. Preferably, a crystallization operation comprising the crystallizing step, the sweating step and the melting step is repeated "n" times to produce the purified (meth)acrylic acid from the crude (meth) acrylic acid, wherein the "n" is an integer 2 or more. Repeating the crystallization operation multiple times allows obtaining the purified (meth)acrylic acid with higher purity. The number of repeating the crystallization operation is preferably 2 to 5 in consideration of efficiently producing the purified (meth)acrylic acid with high purity.

The (meth)acrylic acid melt obtained in the melting step of the $k^{th}$ crystallization operation is utilized as the (meth)acrylic acid solution to be subjected to the crystallizing step of the $k+1^{th}$ crystallization operation, wherein the "k" is an integer 1 or more and, n−1 or less. The (meth)acrylic acid solution containing the crude (meth)acrylic acid is subjected to the crystallizing step of the first crystallization operation, and the (meth)acrylic acid melt obtained in the melting step of the $n^{th}$ crystallization operation is recovered as the purified (meth)acrylic acid, that may be a commercial product. In the below description, the $k^{th}$ crystallization operation may be referred to as a "$k^{th}$ stage".

The residual mother liquid and the sweated liquid obtained at the $k+1^{th}$ stage have lower (meth)acrylic acid concentrations than the (meth)acrylic acid solution subjected to the crystallizing step of the $k+1^{th}$ stage. Therefore, it is preferred that the residual mother liquid and/or the sweated liquid obtained at the $k+1^{th}$ stage is added to the (meth)acrylic acid solution to be subjected to the crystallizing step of the $k^{th}$ or less ordinal stage. That is, it is preferred that the residual mother liquid obtained in the crystallizing step of the $k+1^{th}$ crystallization operation and/or the sweated liquid obtained in the sweating step of the $k+1^{th}$ crystallization operation is added to the (meth)acrylic acid solution to be subjected to the crystallizing step of the $k^{th}$ or less ordinal crystallization operation. In view of utilizing the residual mother liquid and the sweated liquid in the crystallization operation effectively, the residual mother liquid and/or the sweated liquid obtained at the $k+1^{th}$ stage is preferably added to the (meth)acrylic acid solution to be subjected to the crystallizing step of the $k^{th}$ stage. Especially, in view of effective utilization of a polymerization inhibitor contained in the residual mother liquid, it is preferred that the residual mother liquid obtained at the $k+1^{th}$ stage is added to the (meth)acrylic acid solution to be subjected to the crystallizing step of the $k^{th}$ stage.

The amount of the residual mother liquid and the sweated liquid obtained at the $k+1^{th}$ stage added to the (meth)acrylic acid solution subjected to the crystallizing step of the $k^{th}$ stage (or less ordinal stage) is preferably 1 mass % to 50 mass %, more preferably 10 mass % to 40 mass % of the amount of the (meth)acrylic acid solution subjected to the crystallizing step of the $k^{th}$ stage (or less ordinal stage). The concentration of the polymerization inhibitor in the residual mother liquid and the sweated liquid obtained at the $k+1^{th}$ stage is preferably 0.1 times or more and 2.5 times or less, more preferably 0.2 times or more and 2.0 times or less, even more preferably 0.3 times or more and 1.5 times or less of the concentration of the polymerization inhibitor in the (meth)acrylic acid solution subjected to the crystallizing step of the $k^{th}$ stage.

The residual mother liquid and/or the sweated liquid obtained at the first stage is preferably returned to any step preceding the crystallization. As for the residual mother liquid and the sweated liquid obtained at the first stage, it is preferred that the concentration of (meth)acrylic acid is increased by a known purification means such as distillation, diffusion and extraction, and then returned to the step preceding the crystallization. Thereby, impurities contained in the residual mother liquid and the sweated liquid can be discharged from the system of producing process of (meth)acrylic acid. In addition, all or a part of the residual mother liquid and/or the sweated liquid obtained at the first stage may be discharged from the system to be disposed.

As for (meth)acrylic acid, it is known as a polymerizable substance; and therefore, it is preferable that a polymerization inhibitor is added in the crystallization operation for the purpose of preventing polymerization of (meth)acrylic acid to enhance the purity of the obtained purified (meth)acrylic acid and stabilizing the crystallization operation. However, since the polymerization inhibitor contained in the (meth)acrylic acid solution is mostly transferred to the residual mother liquid in the crystallizing step, only a small portion of the polymerization inhibitor is transferred to the (meth)acrylic acid melt obtained in the melting step, whereby polymerization of (meth)acrylic acid easily occurs. Further, when the thus obtained (meth)acrylic acid melt is used as the (meth)acrylic acid solution at the next stage, there is an increased risk of occurring the polymerization of (meth)acrylic acid also at the next stage. Thus, the polymerization inhibitor has been added to at the multiple stages conventionally, thereby complicating the crystallization operation.

Considering the above situation, in the present invention, the (meth)acrylic acid solution subjected to the crystallizing step of the first crystallization operation is made to contain a certain amount of a polymerization inhibitor, and a polymerization inhibitor is not added to the (meth)acrylic acid melt obtained in the melting step of the first to $n-1^{th}$ crystallization operation(s) and the (meth)acrylic acid solution subjected to the crystallizing step of the second to $n^{th}$ crystallization operation(s). In the case where the crystallization operation comprises the sweating step, a polymerization inhibitor is not also added to the sweated liquid obtained in the sweating step of the first to $n^{th}$ crystallization operations. And the concentration of the polymerization inhibitor in the (meth)acrylic acid solution subjected to the crystallizing step of the first crystallization operation is adjusted so that the concentration of the polymerization inhibitor in the (meth)acrylic acid solution subjected to the crystallizing step of the $n^{th}$ crystallization operation is 2 ppm by mass or higher. When the concentration of the polymerization inhibitor in the (meth)acrylic acid solution subjected to the crystallizing step of the $n^{th}$ crystallization operation is 2 ppm by mass or higher, (meth)acrylic acid polymerization reaction is less likely to occur during the period from the crystallizing step of the first stage to the crystallizing step or the sweating step of the $n^{th}$ stage. Thus, according to the producing process of the present invention, the (meth)acrylic acid solution subjected to the crystallizing step of the first crystallization operation is made to preliminarily contain a polymerization inhibitor in the amount required for preventing (meth)acrylic acid polymerization during the period from the crystallizing step of the first stage to the crystallizing step or the sweating step of the $n^{th}$ stage. According to the present invention, since the addition point and concentration of the polymerization inhibitor are set in the above manner, the addition point of the polymerization inhibitor is reduced at minimum, thereby simplifying the crystallization operation, while (meth)acrylic acid polymerization is prevented.

No particular limitation is placed on a method for adjusting the concentration of the polymerization inhibitor in the (meth)acrylic acid solution subjected to the crystallizing step of the first crystallization operation. For example, the polymerization inhibitor may be added to the (meth)acrylic acid solution to be introduced into the crystallizer prior to the first crystallization operation, or the polymerization inhibitor may be introduced into the crystallizer along with the (meth)acrylic acid solution. The polymerization inhibitor may be added at a prior step of obtaining the crude (meth)acrylic acid, that is the step preceding the crystallization, whereby the (meth)acrylic acid solution subjected to the crystallizing step of the first crystallization operation may be made to contain the polymerization inhibitor. Especially, it is efficient that the polymerization inhibitor is added at a prior step of obtaining the crude (meth)acrylic acid in the amount required for preventing polymerization in the crystallization operation, since the effect of preventing polymerization can be obtained also at the prior step. Examples of the prior step include the collection step, the condensation step and the like.

For preventing (meth)acrylic acid polymerization in the crystallization operation, each of the (meth)acrylic acid solution subjected to the crystallizing step of the each crystallization operation only has to contain a polymerization inhibitor in a concentration of 2 ppm by mass or higher. In the case of producing the purified (meth)acrylic acid from the crude (meth)acrylic acid by repeating the crystallization operation multiple times ("n" times in the present invention), the content of the polymerization inhibitor in the (meth)acrylic acid solution decreases as the later crystallization operation which the (meth)acrylic acid solution is subjected to; and hence, it is only necessary that the concentration of a polymerization inhibitor in the (meth)acrylic acid solution subjected to the crystallizing step of the first crystallization operation is adjusted so that the concentration of the polymerization inhibitor in the (meth)acrylic acid solution subjected to the crystallizing step of the $n^{th}$ crystallization operation is 2 ppm by mass or higher. The concentration of the polymerization inhibitor in the (meth)acrylic acid solution subjected to the crystallizing step of the nth crystallization operation is preferably 5 ppm by mass or higher, and more preferably 10 ppm by mass or higher. The upper limit of the concentration of the polymerization inhibitor in the (meth)acrylic acid solution subjected to the crystallizing step of the $n^{th}$ crystallization operation is not particularly limited; however, in view of reducing the addition amount of the polymerization inhibitor, the concentration of that is preferably 50 ppm by mass or lower, and more preferably 25 ppm by mass or lower.

For example, in the case where the residual mother liquid or the sweated liquid generated in the second or the later crystallization operation is added to the (meth)acrylic acid solution subjected to the crystallizing step of the first crystallization operation, the concentration of the polymerization inhibitor in the (meth)acrylic acid solution which the residual mother liquid or the sweated liquid has been added to is regarded as the concentration of the polymerization inhibitor in the (meth)acrylic acid solution subjected to the crystallizing step of the first crystallization operation.

A polymerization inhibitor is not added to the (meth)acrylic acid melt obtained in the melting step of the first to $n-1^{th}$ crystallization operation(s) and the (meth)acrylic acid solution subjected to the crystallizing step of the second to $n^{th}$ crystallization operation(s). Thus, a polymerization inhibitor is not added during the period from the melting step of the first stage to the crystallizing step of the $n^{th}$ stage. In the case where the crystallization operation includes the sweating step, a polymerization inhibitor is not also added to the sweated liquid obtained in the sweating step of the first to $n^{th}$ crystallization operations. Thus, a polymerization inhibitor is not added during the period from the sweating step of the first stage to the sweating step of the $n^{th}$ stage.

It is preferred that the concentration of the polymerization inhibitor in the (meth)acrylic acid solution subjected to the crystallizing step of the first crystallization operation is adjusted higher as the number of times "n", the number of the crystallization operation, increases. As the stage proceeds, the concentration of the polymerization inhibitor in the (meth)acrylic acid solution decreases; and so, in order that the effect of preventing polymerization at the $n^{th}$ stage is exerted surely even when the number of times "n" increases, it is preferred that the concentration of the polymerization inhibitor in the (meth)acrylic acid solution subjected to the crystallizing step of the first crystallization operation is adjusted higher as the number of times "n" increases. Specifically, the relation between the number of times "n" of the crystallization operation and the concentration of the polymerization inhibitor in the (meth)acrylic acid solution subjected to the crystallizing step of the first crystallization operation is preferably defined as follows.

A separation factor $\alpha_k$ in the $k^{th}$ crystallization operation is set, provided that the "k" is an integer 1 or more and n−1 or less; and in the case where the number of times "n" is 2, the concentration of the polymerization inhibitor in the (meth) acrylic acid solution subjected to the crystallizing step of the first crystallization operation is preferably adjusted to be $2 \times \alpha_1$ ppm by mass or higher; in the case where the number of times "n" is 3, the concentration of the polymerization inhibitor in the (meth)acrylic acid solution subjected to the crystallizing step of the first crystallization operation is preferably adjusted to be $2 \times \alpha_1 \times \alpha_2$ ppm by mass or higher; and in the case where the number of times "n" is 4, the concentration of the polymerization inhibitor in the (meth)acrylic acid solution subjected to the crystallizing step of the first crystallization operation is preferably adjusted to be $2 \times \alpha_1 \times \alpha_2 \times \alpha_3$ ppm by mass or higher. Herein, the separation factor $\alpha_k$ is calculated as a ratio $A_k/B_k$, wherein the "$A_k$" is the concentration of the polymerization inhibitor in the (meth)acrylic acid solution subjected to the crystallizing step of the $k^{th}$ crystallization operation and the "$B_k$" is the concentration of the polymerization inhibitor in the (meth)acrylic acid melt obtained in the melting step of the $k^{th}$ crystallization operation. The separation factor $a_k$ varies depending on conditions of the crystallization operation in the each stage, however, it is preferably more than 1.0 and 100 or less, more preferably 1.5 or more and 50 or less, and even more preferably 2.0 or more and 30 or less.

Specific value of the concentration of the polymerization inhibitor in the (meth)acrylic acid solution subjected to the crystallizing step of the first crystallization operation varies depending on the number of times "n" of the crystallization operation and the separation factor $\alpha_k$, and it is exemplified as follows. In the case where the number of times "n" is 2, the concentration of the polymerization inhibitor in the (meth) acrylic acid solution subjected to the crystallizing step of the first crystallization operation is preferably 3 ppm by mass or higher, more preferably 5 ppm by mass or higher, and even more preferably 10 ppm by mass or higher. In the case where the number of times "n" is 3, the concentration of the polymerization inhibitor in the (meth)acrylic acid solution subjected to the crystallizing step of the first crystallization operation is preferably 15 ppm by mass or higher, more preferably 20 ppm by mass or higher, and even more preferably 30 ppm by mass or higher. In the case where the number of times "n" is 4, the concentration of the polymerization inhibitor in the (meth)acrylic acid solution subjected to the crystallizing step of the first crystallization operation is preferably 30 ppm by mass or higher, more preferably 50 ppm by mass or higher, and even more preferably 80 ppm by mass or higher. Regarding the upper limit of the concentration of the polymerization inhibitor in the (meth)acrylic acid solution subjected to the crystallizing step of the first crystallization operation, it is preferably 5 mass % or lower, more preferably 1 mass % or lower, and even more preferably 0.2 mass % or lower, in view of reducing the addition amount of the polymerization inhibitor.

In the case where the number of times "n" is 5 or more, it may need a large amount of the polymerization inhibitor to be added for increasing the polymerization inhibitor concentration in the (meth)acrylic acid solution subjected to the crystallizing step of the first crystallization operation. Therefore, in view of reducing the addition amount of the polymerization inhibitor, the number of times "n" of the crystallization operation is preferably 2, 3 or 4. In respect of ensuring the purity of the obtained purified (meth)acrylic acid, the number of times "n" is more preferably 3 or 4; and considering the balance between reducing the addition amount of the polymerization inhibitor and ensuring the purity of the purified (meth)acrylic acid, it is particularly preferable that the number of times "n" is 3.

In the producing process of the present invention, the (meth)acrylic acid solution subjected to the crystallizing step of the first crystallization operation is made to contain the polymerization inhibitor in a predetermined concentration, and from then on, a polymerization inhibitor is not added prior to the melting step of the $n^{th}$ stage; however, a polymerization inhibitor may be added to the (meth)acrylic acid melt obtained in the melting step of the $n^{th}$ stage. Since the (meth)acrylic acid melt obtained in the melting step of the $n^{th}$ stage becomes a product as the purified (meth)acrylic acid, a polymerization inhibitor is preferably added to the (meth)acrylic acid melt obtained in the melting step of the $n^{th}$ stage for preventing (meth)acrylic acid polymerization in the product and enhancing preservation stability. The concentration of the polymerization inhibitor in the purified (meth)acrylic acid is not particularly limited as long as it is within the range defined as a product specification. The concentration defined as the product specification is preferably 60 ppm by mass or higher and 220 ppm by mass or lower, more preferably 65 ppm by mass or higher and 215 ppm by mass or lower, and even more preferably 70 ppm by mass or higher and 210 ppm by mass or lower, relative to a total amount of the purified (meth)acrylic acid.

In the case where a polymerization inhibitor is added to the (meth)acrylic acid melt obtained in the $n^{th}$ stage, the polymerization inhibitor may be fed into the crystallizer at the melting step of the $n^{th}$ stage, thereby being added to the (meth)acrylic acid melt, or the polymerization inhibitor may be added to the (meth)acrylic acid melt which has been obtained by the melting step of the $n^{th}$ stage and discharged from the crystallizer. The polymerization inhibitor is preferably added to the (meth)acrylic acid melt in the former manner, whereby the effect of preventing (meth)acrylic acid polymerization is enhanced in melting the (meth)acrylic acid crystal in the melting step of the $n^{th}$ stage.

Conventionally-known polymerization inhibitors can be used as the polymerization inhibitor. Examples of the polymerization inhibitor include quinone compounds such as hydroquinone and methoquinone (p-methoxyphenol); phenothiazine compounds such as phenothiazine, bis-(α-methylbenzyl)phenothiazine, 3,7-dioctylphenothiazine and bis-(α-dimethylbenzyl)phenothiazine; N-oxyl compounds such as 2,2,6,6-tetramethylpiperidinooxyl, 4-hydroxy-2,2,6,6-tetramethylpiperidinooxyl and 4,4',4"-tris-(2,2,6,6-tetramethylpiperidinooxyl)phosphite; copper salt compounds such as copper dialkyl dithiocarbamate, copper acetate, copper naphthenate, copper acrylate, copper sulfate, copper nitrate and copper chloride; manganese salt compounds such manganese dialkyl dithiocarbamate, manganese diphenyl dithiocarbamate, manganese formate, manganese acetate, manganese octanoate and manganese naphtenate; nitroso compounds such as N-nitrosophenyl hydroxylamine or salts thereof, p-nitrosophenol and N-nitrosodiphenylamine or salts thereof; and the like. These polymerization inhibitors may be used alone or as a mixture of at least two of them. Among them, at least one kind selected from the group consisting of quinone compounds, N-oxyl compounds, copper salt compounds and manganese salt compounds is preferably used.

In the case of using at least two kinds of polymerization inhibitors, the concentration of the polymerization inhibitor means a sum total of concentrations of the polymerization inhibitors which have been added. For example, in the case where hydroquinone and methoquinone are added as the polymerization inhibitor, the concentration of the polymerization inhibitor means a sum total of mass concentrations of hydroquinone and methoquinone in the (meth)acrylic acid solution.

The process for producing (meth)acrylic acid of the present invention preferably further comprises the step of obtaining the crude (meth)acrylic acid. The step of obtaining the crude (meth)acrylic acid preferably includes a (meth)acrylic acid formation step of obtaining (meth)acrylic acid-containing gas from a (meth)acrylic acid production raw material and a collection step of introducing the (meth)acrylic acid-containing gas into a collection column to be contacted with a liquid medium, thereby obtaining the crude (meth)acrylic acid. In addition, the step of obtaining the crude (meth)acrylic acid may include a condensation step of introducing the (meth)acrylic acid-containing gas into a condensation column to condense, thereby obtaining the crude (meth)acrylic acid, instead of the collection step.

The (meth)acrylic acid production raw material used in the (meth)acrylic acid formation step is not restricted as long as it forms (meth)acrylic acid by reaction, and examples of the (meth)acrylic acid production raw material include, for example, propane, propylene, (meth)acrolein, isobutylene, and the like. Acrylic acid can be obtained by, for example, oxidizing propane, propylene or acrolein in one step, or oxidizing propane or propylene via acrolein in two steps. Acrolein is not limited to that obtained by oxidizing propane or propylene, and acrolein may be formed by dehydration of glycerin. Methacrylic acid can be obtained by, for example, oxidizing isobutylene or methacrolein in one step, or oxidizing isobutylene via methacrolein in two steps. These oxidation reaction and dehydration reaction are preferably carried out in the presence of a catalyst, and conventionally-known catalysts may be used as the oxidation catalyst or the dehydration catalyst for producing (meth)acrylic acid.

In the collection step, the (meth)acrylic acid-containing gas obtained by the (meth)acrylic acid formation step is introduced into a collection column to be contacted with a liquid medium, thereby obtaining the crude (meth)acrylic acid. The (meth)acrylic acid-containing gas introduced into the collection column is contacted with the liquid medium to be collected by the liquid medium. Examples of the liquid medium for collecting the (meth)acrylic acid-containing gas include water, (meth)acrylic acid-containing water, a high boiling point solvent (e.g. diphenyl ether, biphenyl and the like), and the like. The crude (meth)acrylic acid is discharged from a lower part of the collection column (preferably the bottom of the collection column) and can be subjected to the crystallization operation.

In the case where the crude (meth)acrylic acid is obtained by the collection step, the polymerization inhibitor required for the crystallization operation may be introduced into the collection column. The polymerization inhibitor fed to the collection column is discharged from the lower part of the collection column along with the crude (meth)acrylic acid; and therefore, by supplying the polymerization inhibitor to the collection column, the crude (meth)acrylic acid can be made to contain the polymerization inhibitor in the amount required for the crystallization operation. Further, by supplying the polymerization inhibitor in this manner, the effect of preventing polymerization in the collection column can be also obtained. Thus, in the process for producing (meth)acrylic acid of the present invention, it is preferred that the crude (meth)acrylic acid is obtained by introducing (meth)acrylic acid-containing gas into a collection column to be contacted with a liquid medium and the polymerization inhibitor is supplied to the collection column to adjust the concentration of the polymerization inhibitor in the (meth)acrylic acid solution subjected to the crystallizing step of the first crystallization operation. Here, it is preferable that a polymerization inhibitor is not added to the crude (meth)acrylic acid discharged from the collection column, except that the residual mother liquid obtained in the crystallizing step and the sweated liquid obtained in the sweating step is added to the crude (meth)acrylic acid. Thereby, the addition point of the polymerization inhibitor is reduced at minimum and the crystallization operation is simplified.

In the case of employing the condensation step instead of the collection step, the (meth)acrylic acid-containing gas obtained by the (meth)acrylic acid formation step is introduced into a condensation column and cooled to condense (meth)acrylic acid, thereby obtaining the crude (meth)acrylic acid, in the condensation step. For example, a condensate extracted from a middle part of the condensation column can be subjected to the crystallization operation as the crude (meth)acrylic acid.

In addition, a purification step may be provided after the collection step or the condensation step, for the purpose of enhancing the content of (meth)acrylic acid in the crude (meth)acrylic acid obtained by the collection step or the condensation step. In this case, low-quality crude (meth)acrylic acid is obtained in the collection step or the condensation step, and high-quality crude (meth)acrylic acid, which has higher (meth)acrylic acid content than the low-quality crude (meth)acrylic acid, is obtained from the low-quality crude (meth)acrylic acid in the purification step. In the purification step, a known purification means such as distillation, diffusion and extraction may be employed. For example, in the case where distillation is conducted as purification, the low-quality crude (meth)acrylic acid is introduced into a distillation column to obtain the high-quality crude (meth)acrylic acid. The thus obtained high-quality crude (meth)acrylic acid may be subjected to the crystallization operation.

Next, an example embodiment of the producing process of the present invention is explained referring a drawing. FIG. 1 shows a schematic flow for producing the purified (meth)acrylic acid from the crude (meth)acrylic acid by repeating the crystallization operation three times. However, the present invention is not limited to the embodiment shown in the drawing.

In FIG. 1, the first crystallization operation is carried out at S1, the second crystallization operation is carried out at S2, and the third crystallization operation is carried out at S3. (Meth)acrylic acid solutions to be subjected to the crystallization operations S1, S2 and S3 are expressed as A1, A2 and A3, respectively, and (meth)acrylic acid melts obtained in the crystallization operations S1, S2 and S3 are expressed as B1, B2 and B3, respectively. Residual mother liquids and sweated liquids (that are collectively referred to as impurity residual liquids) generated in the crystallization operations S1, S2 and S3 are expressed as C1, C2 and C3, respectively.

A crude (meth)acrylic acid R is discharged from the bottom of a collection column T and subjected to the crystallization operation S1 as the (meth)acrylic acid solution A1. In the crystallization operation S1, a crystallizing step, a sweating step and a melting step are performed, thereby obtaining the (meth)acrylic acid melt B1 and the impurity residual liquid C1. The (meth)acrylic acid melt B1 is subjected to a crystallizing step of the crystallization operation S2 as the (meth) acrylic acid solution A2, and the (meth)acrylic acid melt B2 and the impurity residual liquid C2 are obtained in the same manner. The (meth)acrylic acid melt B2 is subjected to a crystallizing step of the crystallization operation S3 as the (meth)acrylic acid solution A3, and the (meth)acrylic acid melt B3 and the impurity residual liquid C3 are obtained in the same manner. The (meth)acrylic acid melt B3 is handled as a purified (meth)acrylic acid P.

The impurity residual liquids C2, C3 generated in the crystallization operations S2, S3 are respectively added to the (meth)acrylic acid solutions A1, A2 which are to be subjected to the crystallizing steps of the previous crystallization operations S1, S2. Meanwhile, at least a part of the impurity residual liquid C1 generated in the crystallization operation S1 is returned to the collection column T, and herein, it is preferably returned to the collection column T after (meth) acrylic acid content thereof is increased by a known purification means such as distillation, diffusion and extraction. A part of the impurity residual liquid C1 (which may be a purified one) may be extracted from the system to be disposed.

In FIG. 1, a polymerization inhibitor $PI_1$ is added to the crude (meth)acrylic acid R to adjust the concentration of the polymerization inhibitor in the (meth)acrylic acid solution A1. The polymerization inhibitor $PI_1$ is added to the crude (meth)acrylic acid R, but is not added to the (meth)acrylic acid solutions A2, A3 and the (meth)acrylic acid melts B1, B2. Further, the polymerization inhibitor $PI_1$ is not added to the impurity residual liquids C1, C2, C3, too.

As a method for adding the polymerization inhibitor $PI_1$ to the crude (meth)acrylic acid R, the polymerization inhibitor $PI_1$ may be added to at the collection column T, that is expressed as a line X1, and may be added to the crude (meth) acrylic acid R which has been discharged from the collection column T and is to be subjected to the crystallization operation S1, that is expressed as a line X2. On this occasion, the polymerization inhibitor $PI_1$ is added to the crude (meth) acrylic acid R so that the concentration of the polymerization inhibitor in the (meth)acrylic acid solution A3 is 2 ppm by mass or higher.

A polymerization inhibitor $PI_2$ may be added to the (meth) acrylic acid melt B3. Addition of the polymerization inhibitor $PI_2$ to the (meth)acrylic acid melt B3 enhances stability of the purified (meth)acrylic acid P. The polymerization inhibitor $PI_2$ may be introduced into the crystallizer in the melting step of the crystallization operation S3, that is expressed as a line Y1, and may be added to the (meth)acrylic acid melt B3 which has been obtained by the crystallization operation S3 and discharged from the crystallizer, that is expressed as a line Y2. However, in respect of prevention of the polymerization, it is preferred that the polymerization inhibitor $PI_2$ is directly introduced into the crystallizer via the line Y1 in the melting step of the crystallization operation S3.

According to the above producing process of the (meth) acrylic acid, polymerization of (meth)acrylic acid in the crystallization operation is prevented, thereby conducting the crystallization operation stably. Further, the addition point of the polymerization inhibitor is reduced at minimum, thereby simplifying the crystallization operation.

EXAMPLES

The present invention is hereinafter described more specifically by reference to Examples; however, the scope of the present invention is not limited to these Examples.

Producing Example 1

Acrylic acid-containing gas obtained by gas-phase catalytic oxidation reaction of propylene was introduced into a collection column to be made contact with a liquid medium and crude acrylic acid was discharged from the bottom of the collection column. Into the collection column, hydroquinone as a polymerization inhibitor was added. The crude acrylic acid discharged from the bottom of the collection column had composition of 90.0 mass % of acrylic acid, 2.4 mass % of water, 1.9 mass % of acetic acid, 0.6 mass % of maleic acid, 1.5 mass % of acrylic acid dimer and 0.01 mass % (100 ppm by mass) of hydroquinone, and its temperature was 91° C. The crude acrylic acid was cooled to around outside air temperature and then introduced into a crystallizer.

The crystallizer was provided with a metallic crystallization tube, which had a length of 6 m and an inner diameter of 70 mm, and a reservoir (a collector part) at a lower part of the crystallizer. A circulation path connecting the lower part of the crystallizer (the reservoir) to the upper part of the crystallizer (the top of the crystallization tube) was mounted on the crystallizer and provided with a circulation pump. The crystallizer had such mechanisms that a liquid in the reservoir was able to be transferred to the upper part of the tube by the circulation pump and made to flow downward on the inner surface of the crystallization tube in the form of falling film. A double-layered jacket was provided on the outer surface of the crystallization tube and the jacket was controlled so as to keep a constant temperature by a thermostat.

The crude acrylic acid was introduced into the crystallizer and a crystallization operation including a crystallizing step, a sweating step and a melting step was repeated three times to obtain purified acrylic acid. In the crystallizing step, the crude acrylic acid (an acrylic acid solution) was supplied to the crystallizer, and made to flow downward on the inner surface of the crystallization tube in the form of falling film while being circulated between the crystallizer and circulation path. Temperature of the jacket was adjusted to be lower than the melting point of the crude acrylic acid and about 60 mass % to 90 mass % of the crude acrylic acid supplied to the crystallizer was crystallized on the inner surface of the crystallization tube. In the sweating step, operation of the circulation pump was stopped and the temperature of the jacket was raised to higher than the melting point, whereby about 2 mass % to 5 mass % of the acrylic acid crystal was melted. At the end of the sweating step, an uncrystallized residual mother liquid obtained in the crystallizing step and a melt (a sweated liquid) obtained in the sweating step were discharged from the crystallizer. In the melting step, the temperature of the jacket was raised to higher than the melting point, whereby the rest of the acrylic acid crystal was melted to obtain acrylic acid melt. On this occasion, the acrylic acid melt was made to flow downward over the acrylic acid crystal deposited on the inner surface of the crystallization tube while being circulated between the crystallizer and the circulation path. The acrylic acid melt obtained in the melting step of the first crystallization operation was subjected to the crystallizing step of the second crystallization operation as the acrylic acid solution, and the acrylic acid melt obtained in the melting step of the second crystallization operation was subjected to the crystallizing step of the third crystallization operation as the acrylic acid solution. The concentration of the polymerization inhibitor in the acrylic acid solution subjected to the crystallizing step of the third crystallization operation was 15 ppm by mass.

At the melting step of the third crystallization operation, 5 mass % p-methoxyphenol-containing acrylic acid solution, in which p-methoxyphenol was used as a polymerization inhibitor, was fed to the reservoir at the lower part of the crystallizer, and then the melt was made to flow downward over the acrylic acid crystal deposited on the inner surface of the crystallization tube while being circulated between the crystallizer and the circulation path, thereby obtaining the purified acrylic acid. The 5 mass % p-methoxyphenol-containing acrylic acid solution was fed so that p-methoxyphenol was contained in the purified acrylic acid in the concentration of 70 ppm by mass.

In the producing example 1, the purified acrylic acid was produced in the above manner and the operation was conducted continuously for 60 days. During the 60 days' operation, formation of acrylic acid polymers was not observed in the crystallization operation and the crystallization operation was stably conducted.

Producing Example 2

The purified acrylic acid was produced from propylene in the same manner as the producing example 1; however, the amount of the polymerization inhibitor introduced into the collection column was reduced to less than that in the producing example 1. Composition of the crude acrylic acid discharged from the bottom of the collection column was not substantially changed from that in the producing example 1 except hydroquinone, and the content of hydroquinone was 0.004 mass % (40 ppm by mass). A polymerization inhibitor was not added at any step after the collection step and prior to the melting step of the third crystallization operation. As a result, the concentration of the polymerization inhibitor in the acrylic acid solution subjected to the crystallizing step of the third crystallization operation decreased to 5.0 ppm by mass.

In the producing example 2, the purified acrylic acid was produced in this manner and the operation was conducted continuously for 50 days. During the 50 days' operation, formation of acrylic acid polymers was not observed in the crystallization operation and the crystallization operation was stably conducted.

Producing Example 3

The purified acrylic acid was produced from propylene in the same manner as the producing example 1; however, the amount of the polymerization inhibitor introduced into the collection column was reduced to less than that in the producing example 1. Composition of the crude acrylic acid discharged from the bottom of the collection column was not substantially changed from that in the producing example 1 except hydroquinone, and the content of hydroquinone was 0.0015 mass % (15 ppm by mass). A polymerization inhibitor was not added at any step after the collection step and prior to the melting step of the third crystallization operation. As a result, the concentration of the polymerization inhibitor in the acrylic acid solution subjected to the crystallizing step of the third crystallization operation decreased to 2.0 ppm by mass.

In the producing example 3, the purified acrylic acid was produced in this manner and the operation was conducted continuously for 30 days. During the 30 days' operation, formation of acrylic acid polymers was not observed in the crystallization operation and the crystallization operation was stably conducted.

Producing Example 4

The purified acrylic acid was produced from propylene in the same manner as the producing example 1; however, the amount of the polymerization inhibitor introduced into the collection column was reduced to less than that in the producing example 1. Composition of the crude acrylic acid discharged from the bottom of the collection column was not substantially changed from that in the producing example 1 except hydroquinone, and the content of hydroquinone was 0.001 mass % (10 ppm by mass). A polymerization inhibitor was not added at any step after the collection step and prior to the melting step of the third crystallization operation. As a result, the concentration of the polymerization inhibitor in the acrylic acid solution subjected to the crystallizing step of the third crystallization operation decreased to 1.5 ppm by mass.

In the producing example 4, the operation was conducted continuously to produce the purified acrylic acid in the above manner; however, on the 8th day from the beginning of the production, in conducting the melting step of the second crystallization operation, the operation of the pump was stopped due to the polymerization of the acrylic acid melt in the pump.

Producing Example 5

The purified acrylic acid was produced from propylene in the same manner as the producing example 1; however, the amount of the polymerization inhibitor introduced into the collection column was reduced to less than that in the producing example 1. Composition of the crude acrylic acid discharged from the bottom of the collection column was not substantially changed from that in the producing example 1 except hydroquinone, and the content of hydroquinone was 0.0005 mass % (5 ppm by mass). The crude acrylic acid was introduced into the crystallizer and the crystallization operation including the crystallizing step, the sweating step and the melting step was repeated two times to obtain the purified acrylic acid. A polymerization inhibitor was not added at any step prior to the melting step of the second crystallization operation. As a result, the concentration of the polymerization inhibitor in the acrylic acid solution subjected to the crystallizing step of the second crystallization operation was 2.0 ppm by mass. At the melting step of the second crystallization operation, 5 mass % p-methoxyphenol-containing acrylic acid solution was fed to the purified acrylic acid so that p-methoxyphenol was contained in the purified acrylic acid in the concentration of 70 ppm by mass in the same manner as the producing example 1.

In the producing example 5, the purified acrylic acid was produced in this manner and the operation was conducted continuously for 30 days. During the 30 days' operation, formation of acrylic acid polymers was not observed in the crystallization operation and the crystallization operation was stably conducted.

Producing Example 6

The purified acrylic acid was produced from propylene in the same manner as the producing example 1; however, the amount of the polymerization inhibitor introduced into the collection column was reduced to less than that in the producing example 1. Composition of the crude acrylic acid discharged from the bottom of the collection column was not substantially changed from that in the producing example 1 except hydroquinone, and the content of hydroquinone was 0.004 mass % (40 ppm by mass). The crude acrylic acid was introduced into the crystallizer and the crystallization operation including the crystallizing step, the sweating step and the melting step was repeated four times to obtain the purified acrylic acid. A polymerization inhibitor was not added at any step prior to the melting step of the fourth crystallization operation. As a result, the concentration of the polymerization inhibitor in the acrylic acid solution subjected to the crystallizing step of the fourth crystallization operation was 2.0 ppm by mass. At the melting step of the fourth crystallization operation, 5 mass % p-methoxyphenol-containing acrylic acid solution was fed to the purified acrylic acid so that p-methoxyphenol was contained in the purified acrylic acid in the concentration of 70 ppm by mass in the same manner as the producing example 1.

In the producing example 6, the purified acrylic acid was produced in this manner and the operation was conducted continuously for 30 days. During the 30 days' operation, formation of acrylic acid polymers was not observed in the crystallization operation and the crystallization operation was stably conducted.

Acrylic acid producing conditions and operation statuses of the plant in the producing examples 1 to 6 are summarized in Table 1.

TABLE 1

| Producing Example | Number of Crystallization operation | Concentration of Polymerization Inhibitor in Acrylic Acid Solution Subjected to Crystallizing step | | Operation Status of Plant |
|---|---|---|---|---|
| | | First Crystallization operation | Last Crystallization operation | |
| 1 | 3 times | 0.01 mass % | 15 ppm by mass | Stable Operation for 60 days |
| 2 | 3 times | 0.004 mass % | 5.0 ppm by mass | Stable Operation for 50 days |
| 3 | 3 times | 0.0015 mass % | 2.0 ppm by mass | Stable Operation for 30 days |
| 4 | 3 times | 0.001 mass % | 1.5 ppm by mass | Operation was Stopped on 8th day |
| 5 | 2 times | 0.0005 mass % | 2.0 ppm by mass | Stable Operation for 30 days |
| 6 | 4 times | 0.004 mass % | 2.0 ppm by mass | Stable Operation for 30 days |

The invention claimed is:

1. A process for producing (meth)acrylic acid, comprising the step of repeating a crystallization operation "n" times to produce purified (meth)acrylic acid from crude (meth)acrylic acid, provided that the "n" is an integer 2 or more, wherein:

the each crystallization operation comprises a crystallizing step of supplying a (meth)acrylic acid solution to a crystallizer to obtain a (meth)acrylic acid crystal, and a melting step of melting the (meth)acrylic acid crystal to obtain a (meth)acrylic acid melt;

a polymerization inhibitor is not added to the (meth)acrylic acid melt obtained in the melting step of the first to n–1$^{th}$ crystallization operation(s) and the (meth)acrylic acid solution subjected to the crystallizing step of the second to n$^{th}$ crystallization operation(s); and a concentration of a polymerization inhibitor in the (meth)acrylic acid solution subjected to the crystallizing step of the first crystallization operation is adjusted so that a concentration of the polymerization inhibitor in the (meth)acrylic acid solution subjected to the crystallizing step of the n$^{th}$ crystallization operation is 2 ppm by mass or higher.

2. The process for producing (meth)acrylic acid according to claim 1, wherein:

the crystallization operation further comprises a sweating step of partially-melting the (meth)acrylic acid crystal to obtain a sweated liquid and discharging the sweated liquid from the crystallizer prior to the melting step; and a polymerization inhibitor is not added to the sweated liquid obtained in the sweating step of the first to n$^{th}$ crystallization operations.

3. The process for producing (meth)acrylic acid according to claim 1, wherein the concentration of the polymerization inhibitor in the (meth)acrylic acid solution subjected to the crystallizing step of the first crystallization operation is adjusted higher as the number of times "n" increases.

4. The process for producing (meth)acrylic acid according to claim 1, wherein the number of times "n" is 2, 3 or 4, the concentration of the polymerization inhibitor in the (meth)acrylic acid solution subjected to the crystallizing step of the first crystallization operation is adjusted to be $2\times\alpha_1$ ppm by mass or higher in a case where the number of times "n" is 2, the concentration of the polymerization inhibitor in the (meth)acrylic acid solution subjected to the crystallizing step of the first crystallization operation is adjusted to be $2\times\alpha_1\times\alpha_2$ ppm by mass or higher in a case where the number of times "n" is 3, and the concentration of the polymerization inhibitor in the (meth)acrylic acid solution subjected to the crystallizing step of the first crystallization operation is adjusted to be $2\times\alpha_1\times\alpha_2\times\alpha_3$ ppm by mass or higher in a case where the number of times "n" is 4, wherein the "$\alpha_k$" represents a separation factor in the k$^{th}$ crystallization operation, provided that the "k" is an integer 1 or more and n–1 or less, and is calculated as a ratio $A_k/B_k$ wherein the "$A_k$" is the concentration of the polymerization inhibitor in the (meth)acrylic acid solution subjected to the crystallizing step of the k$^{th}$ crystallization operation and the "$B_k$" is the concentration of the polymerization inhibitor in the (meth)acrylic acid melt obtained in the melting step of the k$^{th}$ crystallization operation.

5. The process for producing (meth)acrylic acid according to claim 1, wherein the number of times "n" is 3.

6. The process for producing (meth)acrylic acid according to claim 1, wherein
the crude (meth)acrylic acid is obtained by introducing (meth)acrylic acid-containing gas into a collection column to be contacted with a liquid medium, and
the polymerization inhibitor is supplied to the collection column to adjust the concentration of the polymerization inhibitor in the (meth)acrylic acid solution subjected to the crystallizing step of the first crystallization operation.

7. The process for producing (meth)acrylic acid according to claim 2, wherein
the concentration of the polymerization inhibitor in the (meth)acrylic acid solution subjected to the crystallizing step of the first crystallization operation is adjusted higher as the number of times "n" increases.

8. The process for producing (meth)acrylic acid according to claim 2, wherein
the number of times "n" is 2, 3 or 4,
the concentration of the polymerization inhibitor in the (meth)acrylic acid solution subjected to the crystallizing step of the first crystallization operation is adjusted to be $2 \times \alpha_1$ ppm by mass or higher in a case where the number of times "n" is 2,
the concentration of the polymerization inhibitor in the (meth)acrylic acid solution subjected to the crystallizing step of the first crystallization operation is adjusted to be $2 \times \alpha_1 \times \alpha_2$ ppm by mass or higher in a case where the number of times "n" is 3, and
the concentration of the polymerization inhibitor in the (meth)acrylic acid solution subjected to the crystallizing step of the first crystallization operation is adjusted to be $2 \times \alpha_1 \times \alpha_2 \times \alpha_3$ ppm by mass or higher in a case where the number of times "n" is 4,
wherein the "$\alpha_k$" represents a separation factor in the $k^{th}$ crystallization operation, provided that the "k" is an integer 1 or more and n−1 or less, and is calculated as a ratio $A_k/B_k$ wherein the "$A_k$" is the concentration of the polymerization inhibitor in the (meth)acrylic acid solution subjected to the crystallizing step of the $k^{th}$ crystallization operation and the "$B_k$" is the concentration of the polymerization inhibitor in the (meth)acrylic acid melt obtained in the melting step of the $k^{th}$ crystallization operation.

9. The process for producing (meth)acrylic acid according to claim 2, wherein the number of times "n" is 3.

10. The process for producing (meth)acrylic acid according to claim 2, wherein
the crude (meth)acrylic acid is obtained by introducing (meth)acrylic acid-containing gas into a collection column to be contacted with a liquid medium, and
the polymerization inhibitor is supplied to the collection column to adjust the concentration of the polymerization inhibitor in the (meth)acrylic acid solution subjected to the crystallizing step of the first crystallization operation.

* * * * *